United States Patent [19]

Vlock

[11] Patent Number: 4,961,698

[45] Date of Patent: Oct. 9, 1990

[54] ULTRASONIC DEVICE WITH ADDITIVE CHAMBER

[76] Inventor: David G. Vlock, 12 Fifth Ave., New York, N.Y. 10011-8857

[21] Appl. No.: 367,243

[22] Filed: Jun. 16, 1989

[51] Int. Cl.$^5$ .............................................. A61C 3/08
[52] U.S. Cl. ...................................... 433/86; 433/88; 433/119
[58] Field of Search .......................... 433/86, 88, 119; 128/24 A, 62 A

[56] References Cited

U.S. PATENT DOCUMENTS

| | | | |
|---|---|---|---|
| 2,303,667 | 12/1942 | Taborski | 128/62 A |
| 3,192,922 | 7/1965 | Winkler | 128/62 A |
| 3,956,826 | 5/1976 | Perdreaux, Jr. | 433/86 |
| 4,429,434 | 2/1984 | Sung-shan | 15/167.1 |
| 4,564,005 | 1/1986 | Marchand et al. | 128/66 |
| 4,608,018 | 8/1986 | Ghedini et al. | 433/88 |
| 4,717,057 | 1/1988 | Porteous | 433/163 |
| 4,776,794 | 10/1988 | Meller | 433/88 |

FOREIGN PATENT DOCUMENTS 1270534 4/1972 United Kingdom ............. 128/62 A

Primary Examiner—Cary E. Stone
Attorney, Agent, or Firm—Notaro & Michalos

[57] ABSTRACT

An ultrasonic device includes an auxiliary chamber for receiving an additive in tablet form. The ultrasonic device includes an ultrasonic tool which is connected to an ultrasonic vibrator by a shank. A sleeve surrounds the shank and defines an annular space therewith. Cleansing fluid, in particular water, flows through the annular chamber and exits in the area of the tool. The auxiliary chamber is formed by an axial bore extending through the sleeve and communicating with the annular chamber. A cap closes the outer end of the bore and the bore is dimensioned for receiving a tablet containing the additive. Some of the fluid in the annular chamber passes through the auxiliary chamber to dissolve the tablet and introduce the additive into the stream of fluid before it is discharged at the ultrasonic tool.

16 Claims, 2 Drawing Sheets

ULTRASONIC DEVICE WITH ADDITIVE CHAMBER

FIELD AND BACKGROUND OF THE INVENTION

The present invention relates in general to ultrasonic devices used primarily in dentistry, and in particular to a new and useful ultrasonic device having a chamber for receiving an additive for the ultrasonic cleansing fluid.

An ultrasonic device and method is known from U.S. Pat. No. 3,956,826. That device utilizes an ultrasonic vibrator which vibrates at a frequency range of 10,000 to 40,000 Hertz. A tool assembly for ultrasonically dispersing a cleansing fluid such as water, is connected to the vibrator by a shank. A sleeve encases the shank and defines an annular space therearound. Water which is used as the cleansing fluid is supplied from the vibrator to the annular space which is open near the rear end of the tool assembly. Water passing through the annular space reaches the front end of the tool assembly and is ultrasonically dispersed by the tip of the tool assembly.

The tool assembly, sleeve and a core portion of the vibrator are assembled as a single unit which can be detachably connected to a handle which carries the remainder of the vibrator as well as electrical and hydraulic connections for supplying power and the cleansing fluid.

The ultrasonic device is characterized by its intricate parts and compact design.

SUMMARY OF THE INVENTION

The present invention is directed to a device and method of introducing an additive into the flow of cleansing fluid. This is done without disturbing the functionality of the ultrasonic device or the fact that the tool assembly can be readily inserted and removed from the handle.

According to the present invention, the sleeve of the tool assembly is modified so as to include or be connectable to an auxiliary chamber which communicates with the annular space between the shank which is connected to the ultrasonic tool, and the sleeve surrounding the shank. Means are provided for introducing a tablet into the auxiliary chamber. As cleansing fluid, e.g. water, passes through the annular space, some of the fluid passes through the auxiliary chamber and slowly dissolves the tablet, thereby introducing the additive into the stream of fluid.

The tablet may advantageously include flavorants, antibiotics, sterilizing agents, mouth wash or various medications. Some applications may utilize a so called "disclosing tablet" which contains a dye that adheres to plaque, and thus discloses area where plaque must be removed from the teeth.

Alternatively, additives in powdered, paste or liquid form may me added to the auxiliary chamber.

According to one embodiment of the invention, the auxiliary chamber is formed as a substantially radial bore extending through the sleeve and communicating with the annular space. The bore is closed by a cap which can be snapped, screwed or otherwise sealed to the opening of the bore. To utilize the auxiliary chamber, the cap is removed before the ultrasonic device is activated, and a tablet is introduced into the auxiliary chamber. The cap is then replaced and the ultrasonic device activated for use.

By extending the bore substantially radially through the sleeve, the tablet can be brought into direct contact with the shank. When the ultrasonic device is activated, the tablet is mechanically broken up since it is in contact with the ultrasonically vibrating shank.

The bore may be inclined either rearwardly or forwardly with respect to the axis of the sleeve for either reducing or increasing the rate at which the tablet is dissolved.

According to another embodiment of the invention, a flow constricting ring is engaged around the shank in the area of the auxiliary chamber for deflecting some or all of the fluid flow into the chamber. In this embodiment, the flow constricting ring spans the open bottom of the bore and supports the tablet away from the shank. This reduces the rate at which the tablet breaks up. This is counteracted by the more active flow of fluid through the chamber which efficiently dissolves the tablet and adds its contents to the flow of fluid.

In a still further embodiment of the invention, the auxiliary chamber is constructed as a separate unit which includes an inlet line and an outlet line. The inlet line is connected to the sleeve for receiving an inflow of fluid from the annular space. The outlet line is connected to a sleeve at a spaced location from the inlet line and discharges the fluid plus dissolved additive into the flow. A flow constricting ring can also be utilized in this embodiment for diverting some or all of the fluid through the auxiliary chamber.

Accordingly an object of the present invention is to provide a mechanism for including an additive in the flow of ultrasonic cleansing fluid passing through an ultrasonic device.

A further object of the present invention is to include an auxiliary chamber in the ultrasonic device without reducing the operability and efficiency of the device and while maintaining the interchangeability of the tool assembly with the handle of the device.

A still further object of the invention is to provide an ultrasonic device with additive chamber which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFFERED EMBODIMENTS

Figure 1:
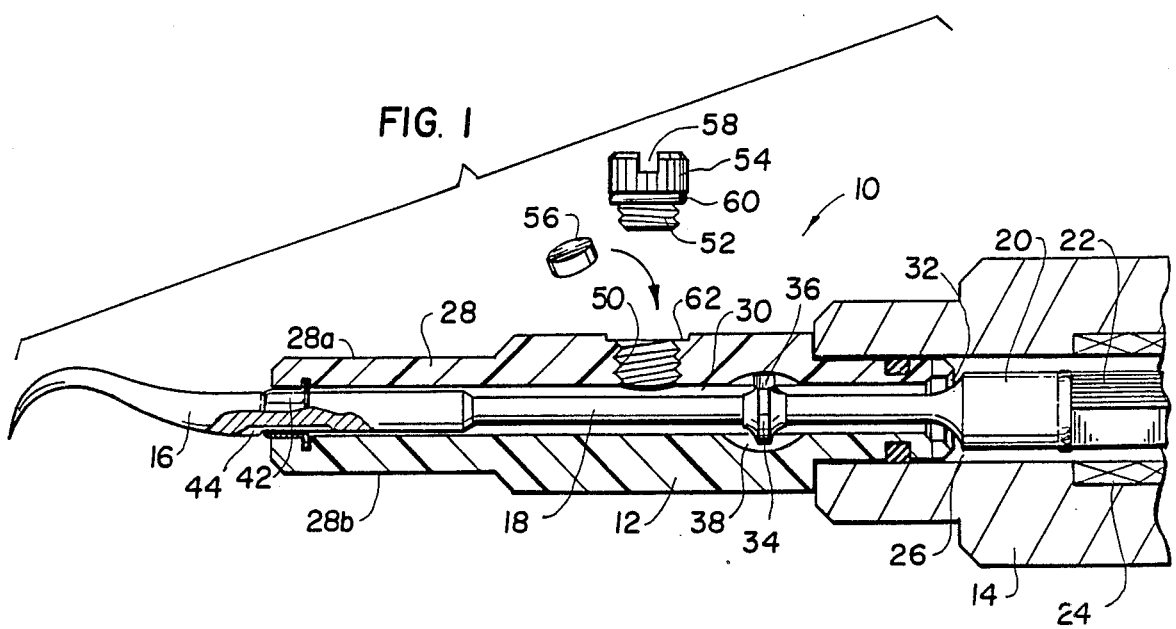
FIG. 1 is a partial, longitudinal sectional view of an ultrasonic device with auxiliary chamber in accordance with the present invention.

Referring to the drawings in particular, the invention embodied in FIG. 1 comprises an ultrasonic device generally designated 10 which comprises a handle assembly 14 for detachably receiving an insert assembly 12. The insert assembly includes a tool 16 having a curved tip for use in dental cleaning procedures. A shank 18 is integrally connected to the tool 16 and to a connecting body 20. A plurality of metallic plates 22 are brazed or otherwise connected to the body 20. A coil 24 is seated in the interior of handle 14 and positioned around the plates 22. Coil 24 is activated, in a known manner, by current which alternates at ultrasonic frequencies for ultrasonically vibrating plate 22. The ultrasonic vibrations are transmitted over body 20 and shank 18 to the tool 16.

Cleansing fluid, in particular water, is supplied to a supply chamber 26 in handle 14 in a manner (not shown) which is known in the art.

The insert assembly 12 includes a sleeve 28 which is advantageously assembled of two substantially identical sleeve halves 28a and 28b. The sleeve halves are welded, glued or otherwise permanently connected to each other around the shank 18. The inside diameter of sleeve 28 is selected to be larger than the maximum outside diameter of shank 18. This forms an annular chamber 30 which communicates with the supply chamber 26 through an annular inlet passage 32 defined between the rear end of sleeve 28 and the connector 20.

Figure 6:
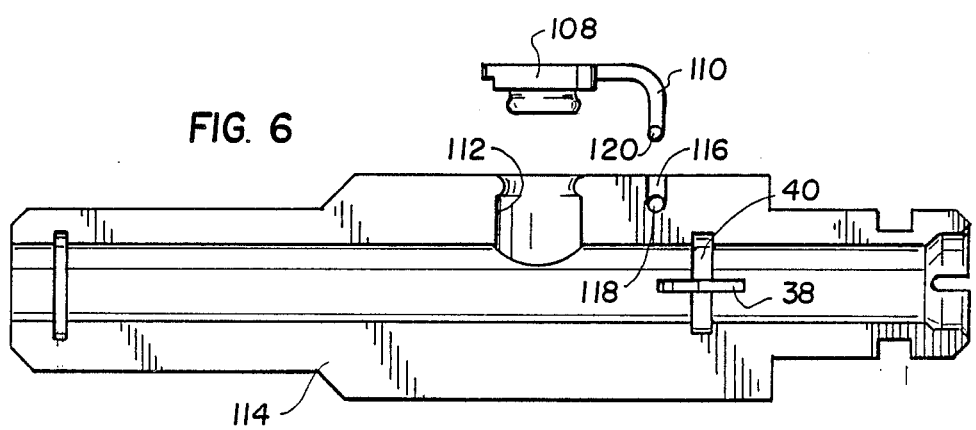
FIG. 6 is a plan view of half of the sleeve of an ultrasonic device which incorporates an embodiment of the present invention.

In order to fix sleeve 28 to shank 18, shank 18 carries a ring 34 which is seated in a groove in sleeve 28. To prevent any relative rotation between shank 18 and sleeve 28, a key 36 extends radially outwardly from ring 34 and is seated within one of a pair of longitudinally extending semi-circular grooves 38. As best shown in FIG. 6 which is plan view of one sleeve half, groove 38 communicates with an annular groove 40 which receives the ring 34. Grooves 38 act as a passage for fluid past the ring 34, in the annular chamber 30.

A bushing 42 embraces the shank 18 near tool 16 and defines an annular nozzle for the discharge of water from the annular chamber 30 to an area around the ultrasonic tool 16. A longitudinal notch 44 is cut into the material of the shank 18 near the tool 16 for an additional spray of water from the chamber 30.

The functioning of the ultrasonic tool 10 for conveying cleansing fluid, and in particular water, from the handle through the insert assembly and to the tool is fully disclosed in the above-identified U.S. Pat. No. 3,956,826.

As is evident from FIG. 1, little space is available in the annular chamber 30 for introducing any type of additive. It is however, most advantageous to provide an additive in the area of the insert assembly to avoid any modifications to the handle assembly 14. This is because the insert assembly 12 is meant to be a replaceable and interchangeable part which can be cleansed, sterilized and replaced as needed.

According to the present invention, one of the sleeve halves 28a is provided with a radially extending bore 50 which, in the embodiment of FIG. 1, is threaded for receiving the threaded shank 52 of a cap 54. Shank 52 is shorter than the radial length of bore 50 to leave space within the bore for defining an auxiliary chamber which communicates with the annular chamber 30. A tablet 56 can thus be introduced into bore 50. The open end of bore 50 is then closed by cap 54. Advantageously cap 54 has a knurled periphery and may include a slot 58 for receiving a screw driver bit, a coin or the like.

In order to hermetically seal bore 50, an O-ring 60 is provided around the shank 52 under the head of the cap. When the shank 52 is screwed into the bore 50, O-ring 60 is firmly seated against a flat area 62 which has been machined into the surface of the otherwise cylindrical sleeve 28.

Figure 2:
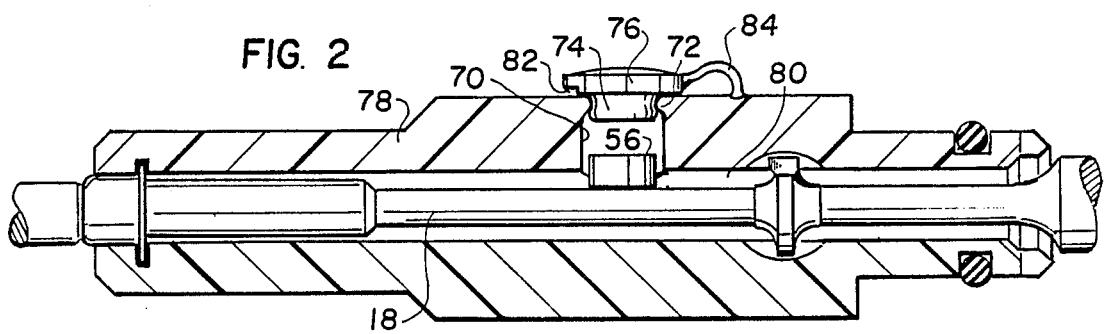
FIG. 2 is a longitudinal sectional view of a sleeve and shank portion of a ultrasonic device on an enlarged scale, showing another embodiment of the invention.

An alternate embodiment of the invention is shown in FIG. 2 where a radial bore 70 is formed in one half of the sleeve 78 for communicating with the annular chamber 80. An annular projection 72 is formed in the open end of the bore 70 and is engaged by an annular groove 74 in the cap 76. By making cap 76 of resilient plastic material, the engagement of groove 74 onto projection 72 forms a hermetic seal to close chambers 70 and 80 from the exterior. Tablet 56 is shown in a position directly touching the shank 18 of the ultrasonic tool. When the ultrasonic tool is activated, tablet 56 tends to break up, thus enhancing the inclusion of additives into the flow of fluid through chamber 80. A step 82 is advantageously formed under the head of cap 76 for engagement by a fingernail or the like to aid in the lifting of cap 76 out of bore 70. A tether 84 is also integrally formed with cap 76 and may be integrally connected to the sleeve 78, which itself is made of plastic.

Figure 3:
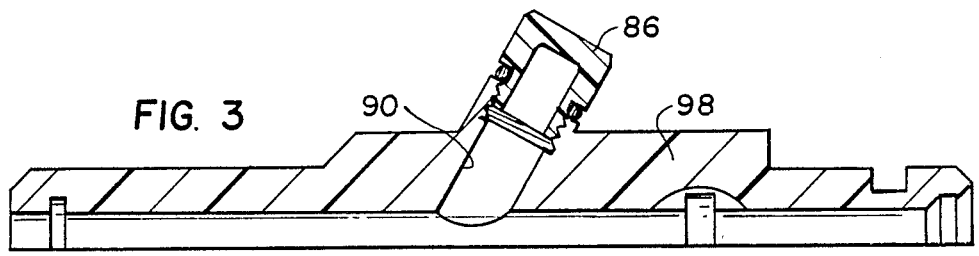
FIG. 3 is a sectional view of half of the sleeve of an ultrasonic device including the present invention.
Figure 4:
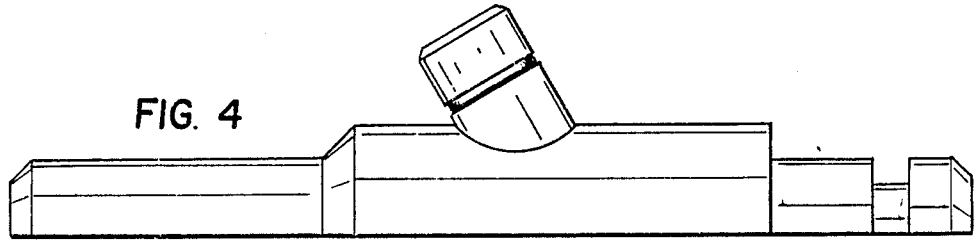
FIG. 4 is a side elevational view showing another embodiment of the invention which is similar to that of FIG. 3.

The embodiment of FIGS. 3 and 4 differ from those of FIGS. 1 and 2 in that the auxiliary chamber if formed by a bore that while being substantially radial in extent, is inclined at an angle to the longitudinal axis of the device. In the embodiment of FIG. 3, the bore 90 while communicating with the annular chamber defined in the sleeve 98, is inclined rearwardly with respect to the tool end of the device. This reduces the tendency of fluid to flow into the auxiliary chamber thus lowering the rate at which a tablet or other additive in the chamber will dissolve and be introduced into the stream. Bore 90 is closed by a cap 86 which is threaded into the bore and which includes a hollow space for receiving a tablet or other additive. According to this embodiment of the invention, cap 86 can be removed and inverted for receiving the additive tablet, or the additive in paste, powder or liquid form. Cap 86 is then introduced into bore 90 and sealed thereto.

The embodiment in FIG. 4 operates in substantially the same way as that of FIG. 3. By inclining the bore forwardly with respect to the longitudinal axis however, the flow of fluid which, in the Figures is from right to left, is more actively introduced into the auxiliary chamber. This increases the rate at which additive is introduced into the fluid stream.

Figure 5:
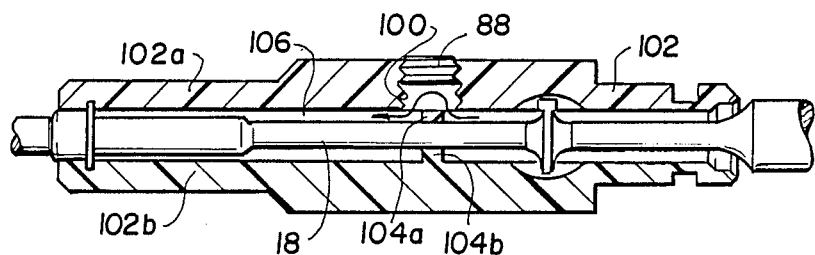
FIG. 5 is a longitudinal sectional view of the sleeve and part of the shank in a tool assembly of an ultrasonic device with another embodiment of the invention.

FIG. 5 shows a further embodiment of the invention which is similar to that of FIG. 1. In the embodiment of FIG. 5, a cap 88 which is shaped somewhat like a set screw, is entirely threaded into the threaded bore 100 which forms the auxiliary chamber. A slot may be provided in the outer surface of cap 88 for engagement by a screw driver or coin for introducing and removing the cap into and from the bore.

The sleeve 102 which includes sleeve halves 102a and 102b which are permanently connected to each other, includes a constricting ring having ring halves 104a and 104b, which closely engages around the shank 18. This constrains the fluid in annular chamber 106 to flow through the auxiliary chamber formed by bore 100. Since the ring portion 104a spans the inside opening of bore 100 and acts to support a tablet within the auxiliary chamber. The tablet is thus kept out of direct contact with the shank 18 thereby reducing its tendency to be broken up. The tablet will dissolve however in the fluid which is constrained to move through the auxiliary chamber.

FIG. 6 shows an embodiment of the invention which includes a cap 108 with tether 110 which is similar in construction to the cap and tether in FIG. 2. In the embodiment of FIG. 6 however, one half of the bore 112 is formed in each of the sleeve halves (only one sleeve half 114 being shown in FIG. 6). When the sleeve halves are connected to each other, a cylindrical bore is formed by the bore halves 114. Sleeve half 114 is also formed with a slot 116 shaped to receive the end of tether 110, and a blind bore 118 shaped to receive one of a pair of trunnions 120, extending from opposite sides of the tether 110. In this way, the end of tether 110 can be captured within the slots and blind bores 116, 118 of the sleeve halves before they are fixed to each other, to permanently connect the cap 108 to the sleeve.

In the embodiments of FIGS. 1 through 6, the auxiliary bore is positioned at a location spaced away from the ring 34 which secures the shank 18 to the interior of the sleeve. As disclosed in U.S. Pat. No. 3,956,826, ring 34 is positioned at a nodal point of the ultrasonic vibrations in shank 18. By positioning the bore which forms the auxiliary chamber at a location spaced from this nodal point, the additive is subjected to ultrasonic vibrations which help disperse the additive into the fluid.

Figure 7:
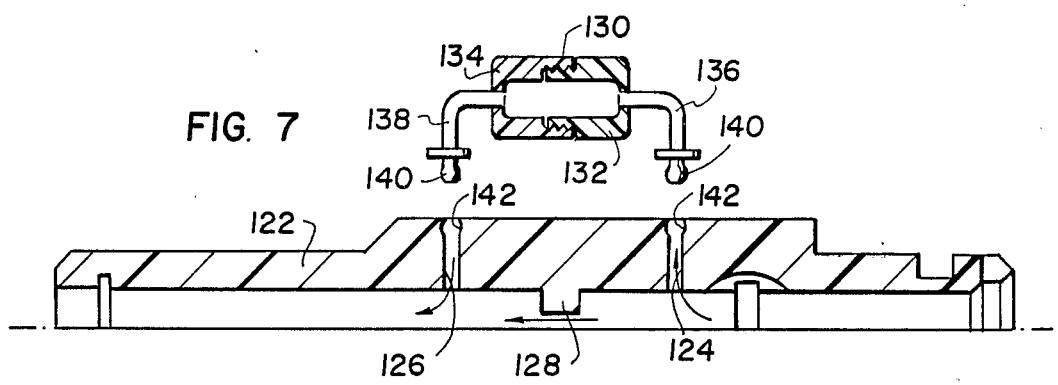
FIG. 7 is a view similar to FIG. 3 showing a further embodiment of the present invention.

FIG. 7 illustrates a still further embodiment of the invention which includes a sleeve half 122. An inlet bore 124 extends radially through the sleeve half and communicates with the annular chamber between the sleeve and the tool shank (not shown). A radially extending outlet bore 126 is spaced away from the inlet bore 124. A constricting ring half 128 is provided on the inner surface of sleeve half 122. Ring half 128 can be structures to extend either fully or only partly to the tool shank for partly or fully constricting the flow of fluid thereacross.

The auxiliary chamber in the embodiment of FIG. 7 is formed by a capsule 130 having a first hollow capsule portion 132 which is threaded to a second hollow portion 134. The hollow space in capsule 130 can thus be opened to receive a tablet or other additive. An inlet conduit 136 is fixed to capsule half 132 and an outlet conduit 138 is fixed to capsule half 134. Each of the inlet and outlet conduits have a bulbous end 140 which can be snap fit into an enlargement 142 at the open end of bores 124 and 126. Conduits 136 and 138 are advantageously flexible so that despite the relative rotational position between the capsule halves 132, 134, the conduits 136, 138 can be bent for introducing their bulbous ends into the enlargements of the bores.

While the inclusion of tablets or additives in other forms for including flavorants, mouth wash and the like is useful, a particularly important use for the invention is to introduce a disinfectant tablet into the auxiliary chamber. The function of the disinfectant tablet would be to disinfect aerosols which come from the patient's mouth during the cleaning procedure using the ultrasonic device. Such aerosols, which are emitted in copious quantity during the procedure, may contain infectious substances from the patient including but not limited to HIV, Herpes or other viruses and contagions which have become an ever increasing threat to dental personnel.

While specific embodiments of the invention have been shown and described in detail to illustrate the application of the principles of the invention, it will be understood that the invention may be embodied otherwise without departing from such principles.

What is claimed:

1. An ultrasonic device for use with a cleansing fluid and additive comprising:

a handle assembly having a supply chamber and carrying first ultrasonic means for causing ultrasonic vibrations;

an insert assembly detachably engaged with said handle assembly and including a portion for insertion into said supply chamber;

said insert assembly comprising a tool, a shank connected to said tool and second ultrasonic means connected to said shank and operable with said first ultrasonic means to ultrasonically vibrate said shank and tool, said insert assembly including a sleeve engaged around said shank and defining an annular chamber with said shank, said annular chamber having an inlet end communicating with said supply chamber and an output end communicating with said tool, said shank including a nodal point and said shank being fixed to said sleeve at said nodal point;

auxiliary chamber means connected to said sleeve and defining an auxiliary chamber communicating with said annular chamber for receiving an additive for introducing the additive into a flow of cleansing fluid passing through said annular chamber and into said auxiliary chamber, said auxiliary chamber means comprising a substantially radial bore through said sleeve opening into said annular chamber for exposing said shank, said bore being spaced away from said nodal point and;

closure means connected to said auxiliary chamber means for opening said auxiliary chamber for introduction of an additive thereto and for closing said auxiliary chamber to prevent loss of fluid through said auxiliary chamber, said closure means comprising a cap for closing an outer end of said bore.

2. A device according to claim 1, wherein said bore extends at an acute angle to an axis of said annular chamber.

3. A device according to claim 1, wherein said cap includes a threaded stem and said bore is threaded for threadably receiving said stem.

4. A device according to claim 3, including an O-ring seal engaged around said stem for sealing said cap to said sleeve.

5. A device according to claim 1, wherein said cap includes a stem, one of said stem and bore including an annular projection and the other of said stem and bore including an annular groove for receiving said annular projection for sealing said cap to said sleeve.

6. A device according to claim 5, including a tether connected between said cap and said sleeve.

7. A device according to claim 1, wherein said device includes, in combination, an additive tablet disposed in said auxiliary chamber and in contact with said shank.

8. A device according to claim 1, wherein said cap is hollow for receiving the additive.

9. A device according to claim 1, wherein said sleeve comprises a pair of sleeve halves which are fixed to each other around said shank, said bore extending through at least one of said sleeve halves.

10. A device according to claim 9, wherein said bore is defined between said pair of sleeves.

11. A device according to claim 9 including a tether fixed between said cap and at least one of said sleeve halves for connecting said cap to said sleeve when said bore is open.

12. A device according to claim 11, wherein said bore is defined between said pair of sleeves, said tether being connected between said pair of sleeves.

13. An ultrasonic device for use with a cleansing fluid and additive comprising:

a handle assembly having a supply chamber and carrying first ultrasonic means for causing ultrasonic vibrations;

an insert assembly detachably engaged with said handle assembly and including a portion for insertion into said supply chamber;

said insert assembly comprising a tool, a shank connected to said tool and second ultrasonic means connected to said shank and operable with said first ultrasonic means to ultrasonically vibrate said shank and tool, said insert assembly including a sleeve engaged around said shank and defining an annular chamber with said shank, said annular chamber having an inlet end communicating with said supply chamber and an output end communicating with said tool;

auxiliary chamber means connected to said sleeve and defining an auxiliary chamber communicating with said annular chamber for receiving an additive for introducing the additive into a flow of cleansing fluid passing through said annular chamber and into said auxiliary chamber; and closure means connected to said auxiliary chamber means for opening said auxiliary chamber for introduction of an additive thereto and for closing said auxiliary chamber to prevent loss of fluid through said auxiliary chamber;

said auxiliary chamber means comprising a substantially radial bore through said sleeve into said annular chamber, said closure means comprising a cap for closing an outer end of said bore; and a constricting ring connected to said sleeve and spanning an interior end of said bore which communicates with said annular chamber whereby fluid passing through said annular chamber is constricted to flow through said auxiliary chamber past said constricting ring.

14. An ultrasonic device for use with a cleansing fluid and additive comprising:

a handle assembly having a supply chamber and carrying first ultrasonic means for causing ultrasonic vibrations;

an insert assembly detachably engaged with said handle assembly and including a portion for insertion into said supply chamber;

said insert assembly comprising a tool, a shank connected to said tool and second ultrasonic means connected to said shank and operable with said first ultrasonic means to ultrasonically vibrate said shank and tool, said insert assembly including a sleeve engaged around said shank and defining an annular chamber with said shank, said annular chamber having an inlet end communicating with said supply chamber and an output end communicating with said tool;

auxiliary chamber means connected to said sleeve and defining an auxiliary chamber communicating with said annular chamber for receiving an additive for introducing the additive into a flow of cleansing fluid passing through said annular chamber and into said auxiliary chamber; and closure means connected to said auxiliary chamber means for opening said auxiliary chamber for introduction of an additive thereto and for closing said auxiliary chamber to prevent loss of fluid through said auxiliary chamber;

said auxiliary chamber means comprising a capsule for containing said auxiliary chamber, said closure means comprising means for opening said capsule for introduction of an additive into said auxiliary chamber, said sleeve including spaced apart inlet and outlet bores each communicating with said annular chamber, said capsule including conduit means for connection to said inlet and outlet bores for receiving a flow of fluid from an annular chamber and through said auxiliary chamber.

15. A device according to claim 14, including a constricting ring connected to said sleeve between said inlet and outlet bores, said constricting ring extending toward said shank for restricting a flow of fluid past said shank and for increasing a flow fluid through said auxiliary chamber.

16. A device according to claim 14, including snap engagement means connected between said conduit means and said bores for fixing said conduit means to said bores.

* * * * *